United States Patent [19]

Weeks

[11] Patent Number: Plant 5,854

[45] Date of Patent: Jan. 13, 1987

[54] ROSE PLANT NAMED CORPUS CHRISTI

[76] Inventor: O. L. Weeks, 926 W. Philadelphia, Ontario, Calif. 91761

[21] Appl. No.: 698,224

[22] Filed: Feb. 4, 1985

[51] Int. Cl.[4] ..... A01H 5/00

[52] U.S. Cl. ..... Plt./20

[58] Field of Search ..... Plt./20-21

*Primary Examiner*—R. E. Bagwill

*Attorney, Agent, or Firm*—Vincent G. Gioia

[57] ABSTRACT

A new cardinal red colored hybrid tea rose variety.

1 Drawing Figure

The present invention relates to a new and distinct variety of rose plant of the hybrid tea rose class, which was originated by my crossing as seed parent an unnamed, unpatented seedling of my creation and the rose known as "Night Time" (U.S. Plant Pat. No. 3,924) as pollen parent. The denomination of this new rose is "Corpus Christi".

Among the novel characteristics possessed by this new variety which distinguish it from its parents and all other varieties of which I am aware are its attractive, large, bright cardinal red flowers borne singly, one to a stem, produced on a very vigorous plant. Flowers are useful for cutting as well as garden decoration. Asexual reproduction by budding of the new variety as performed in San Bernardino County, Calif. shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The terminology used in color description herein refers to plate numbers in the aforementioned color chart, e.g., "60A" is plate 60A of The Royal Horticultural Society Colour Chart.

Parentage: Seedling.

*Seed parent.*—Unnamed Seedling.

*Pollen parent.*—"Night Time".

Class: Hybrid Tea.

The following observations are made of specimens grown outdoors in San Bernardino County, Calif. during the month of October.

FLOWER

Blooming Habit: Recurrent.

A. Bud:

(1) *Size.*—Medium.

(2) *Form.*—Short pointed.

(3) *Color.*—As sepals divid . buds are near 187B. After sepals separate, bud color tends to near 60A.

(4) *Sepals.*—Slightly longer than bud.

(5) *Peduncle.*—Length — long. Aspect — upright, small prickles. Strength — erect, strong. Color — reddish purple and green.

B. Bloom:

(1) *Size.*—Average size when fully expanded — about 5 to 6 inches.

(2) *Borne.*—Singly, one to a stem.

(3) *Form.*—High centered at first, becomes somewhat balled in center as bud starts to open to about ¾ open then somewhat flat, petals large and roll loosely outward.

(4) *Petalage.*—Number of petals under normal conditions — about 25 to 30.

(5) *Color.*—After sepals fall, flower color appears near 46B through 46D with silvery reverse on petaloids. Color remains substantially stable to maturity.

C. Petals:

(1) *Texture.*—Thick.

(2) *Appearance.*—Inside velvety and outside satiny.

(3) *Form.*—Wide ovate, very large.

(4) *Arrangement.*—Regular.

(5) *Petaloids in Center.*—Few.

(6) *Persistence.*—Drop off cleanly.

(7) *Fragrance.*—Slight.

(8) *Lasting quality.*—Long lasting quality on plant and as cut flower.

REPRODUCTIVE ORGANS

A. Stamens, filaments and anthers:

*Arrangement and color.*—Clustered heavily around styles, pinkish red.

B. Pollen:

*Color.*—Pale yellow.

C. Styles: Uneven.

D. Stigmas:

*Color.*—Reddish.

E. Hips: None observed.

PLANT

A. Form: Upright, compact.

B. Growth: Very vigorous.

*Height attained.*—About 5 to 6 feet.

C. Foliage: Compound 5 and 7 leaflets.

(1) *Size.*—Large.

(2) *Quantity.*—Abundant.

(3) *Color.*—New foliage. Upper side — near to 147B to C with overlay of reddish color. Under side — near to 147C with reddish overlay. Old foliage: Upper side — near 147A to B. Under side — near to 147C.

(4) *Shape.*—Ovate.
(5) *Texture.*—Upper side is leathery and under side is matte and veined.
(6) *Edge.*—Serrate.
(7) *Serration.*—Regular.
(8) *Leaf stem.*—Color — near to 147C. Under side — near 147C.
(9) *Stipules.*—Medium.
(10) *Resistance to disease.*—Average.

D. Wood:
(1) *New wood.*—Color — near 147B to C. Bark — smooth.
(2) *Old wood.*—Color — near 147B. Bark — smooth.

E. Thorns:

(1) *Thorns.*—Quantity (main stalk and laterals) — many. Form — long, narrow. Length — medium. Color — reddish, light green. Position — irregular.
(2) *Prickles.*—Many.

F. Winter hardiness: Needs winter protection in severe climate.

I claim:

1. A new and distinct variety of rose plant of the hybrid tea rose class, substantially as shown and described, characterized particularly by large, bright cardinal red flowers which retain color well upon aging borne one to a stem on a very vigorous plant.

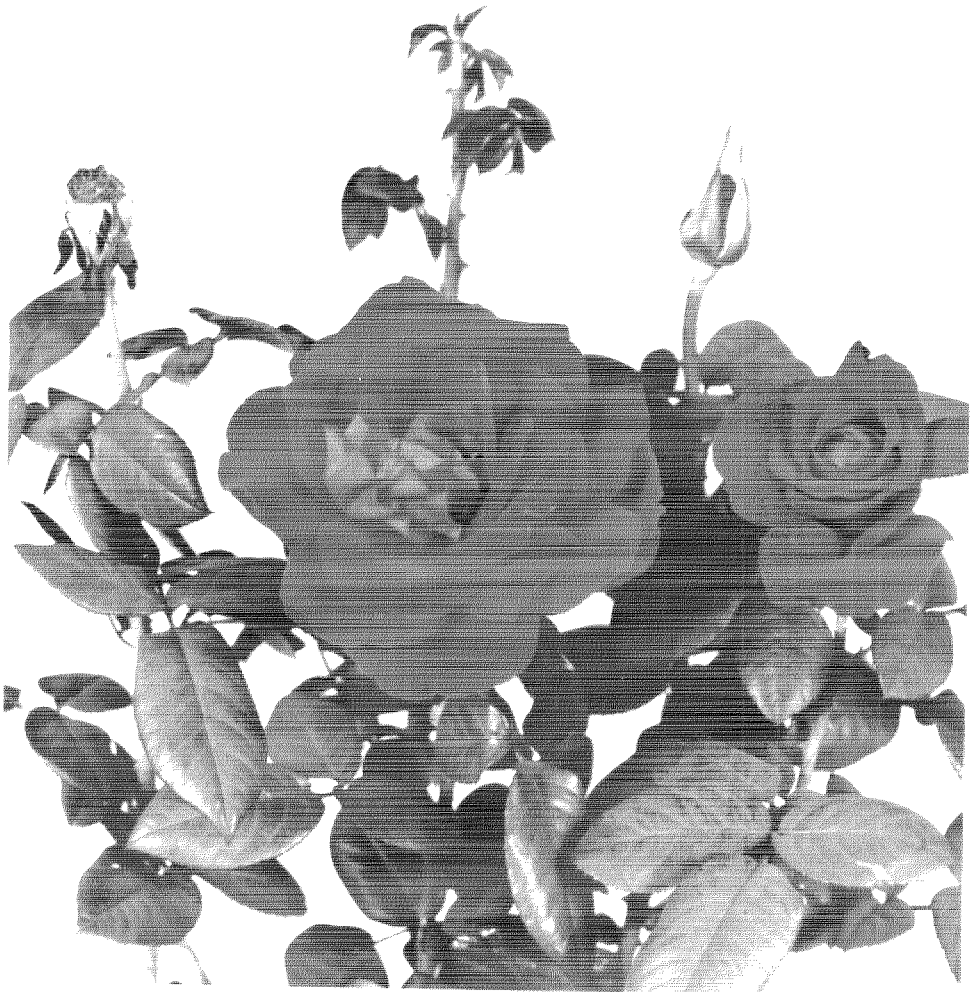

* * * * *